US012622651B2

(12) United States Patent
Montgomery et al.

(10) Patent No.: US 12,622,651 B2
(45) Date of Patent: *May 12, 2026

(54) AUTOREGULATION STATUS MONITORING

(71) Applicant: Covidien LP, Mansfield, MA (US)

(72) Inventors: Dean Montgomery, Edinburgh (GB);
Paul S. Addison, Edinburgh (GB);
Andre Antunes, Edinburgh (GB)

(73) Assignee: Covidien LP, Mansfield, MA (US)

( * ) Notice: Subject to any disclaimer, the term of this patent is extended or adjusted under 35 U.S.C. 154(b) by 842 days.

This patent is subject to a terminal disclaimer.

(21) Appl. No.: 17/514,827

(22) Filed: Oct. 29, 2021

(65) Prior Publication Data

US 2022/0047225 A1 Feb. 17, 2022

Related U.S. Application Data

(63) Continuation-in-part of application No. 16/204,061, filed on Nov. 29, 2018, now Pat. No. 11,202,580.

(51) Int. Cl.
| | |
|---|---|
| *A61B 5/021* | (2006.01) |
| *A61B 5/00* | (2006.01) |
| *G06T 11/00* | (2006.01) |
| *A61B 5/026* | (2006.01) |

(52) U.S. Cl.
CPC ............. *A61B 5/743* (2013.01); *A61B 5/748* (2013.01); *G06T 11/001* (2013.01); *A61B 5/021* (2013.01); *A61B 5/026* (2013.01); *G06T 2200/24* (2013.01); *G06T 2210/41* (2013.01)

(58) Field of Classification Search
CPC ......... A61B 5/743; A61B 5/748; A61B 5/021; A61B 5/026; A61B 5/4035; A61B 5/7275; A61B 5/0215; A61B 5/1455; A61B 5/721; A61B 5/02028; G06T 11/001; G06T 2200/24; G06T 2210/41; G06T 11/206

See application file for complete search history.

(56) References Cited

U.S. PATENT DOCUMENTS

| | | | |
|---|---|---|---|
| 6,475,153 | B1 | 11/2002 | Khair et al. |
| 6,599,251 | B2 | 7/2003 | Chen et al. |
| 9,861,317 | B2 | 1/2018 | Ochs |
| 11,202,580 | B2 | 12/2021 | Addison et al. |
| 2009/0326386 | A1 | 12/2009 | Sethi et al. |

(Continued)

OTHER PUBLICATIONS

Montgomery et al., "Real-Time Intraoperative Determination and Reporting of Cerebral Autoregulation State Using Near-Infrared Spectroscopy," Original Clinical Research Report, Technology, Computing and Simulation, vol. 131, No. 5, Nov. 2020, pp. 1520-1528.

(Continued)

*Primary Examiner* — Andrey Shostak
(74) *Attorney, Agent, or Firm* — Dymera IP, LLC

(57) ABSTRACT

Processing circuitry may receive one or more signals of a patient. The processing circuitry may determine an autoregulation status of the patient based at least in part on the one or more signals. The processing circuitry may output, for display at an output device, a graphical user interface (GUI) that includes an indication of the autoregulation status of the patient and an indication of a lower limit of autoregulation (LLA) value, wherein the GUI does not include an indication of an upper limit of autoregulation (LLA) value.

14 Claims, 5 Drawing Sheets

(56)  References Cited

U.S. PATENT DOCUMENTS

| | | | |
|---|---|---|---|
| 2011/0105927 A1 | 5/2011 | Greenhut et al. | |
| 2012/0136605 A1 | 5/2012 | Addison et al. | |
| 2012/0198386 A1 | 8/2012 | Hautala | |
| 2016/0345913 A1* | 12/2016 | Montgomery | G16Z 99/00 |
| 2017/0105631 A1* | 4/2017 | Addison | A61B 5/7425 |
| 2017/0105672 A1* | 4/2017 | Addison | G16H 40/63 |
| 2018/0014791 A1 | 1/2018 | Montgomery et al. | |
| 2018/0078155 A1 | 3/2018 | Baek et al. | |
| 2018/0338731 A1 | 11/2018 | Addison et al. | |
| 2020/0129076 A1 | 4/2020 | Montgomery et al. | |
| 2020/0187866 A1 | 6/2020 | Antunes et al. | |

OTHER PUBLICATIONS

Prosecution History from U.S. Appl. No. 16/204,061, now U.S. Pat. No. 11,202,580, dated Apr. 20, 2021 through Aug. 16, 2021, 50 pp.

\* cited by examiner

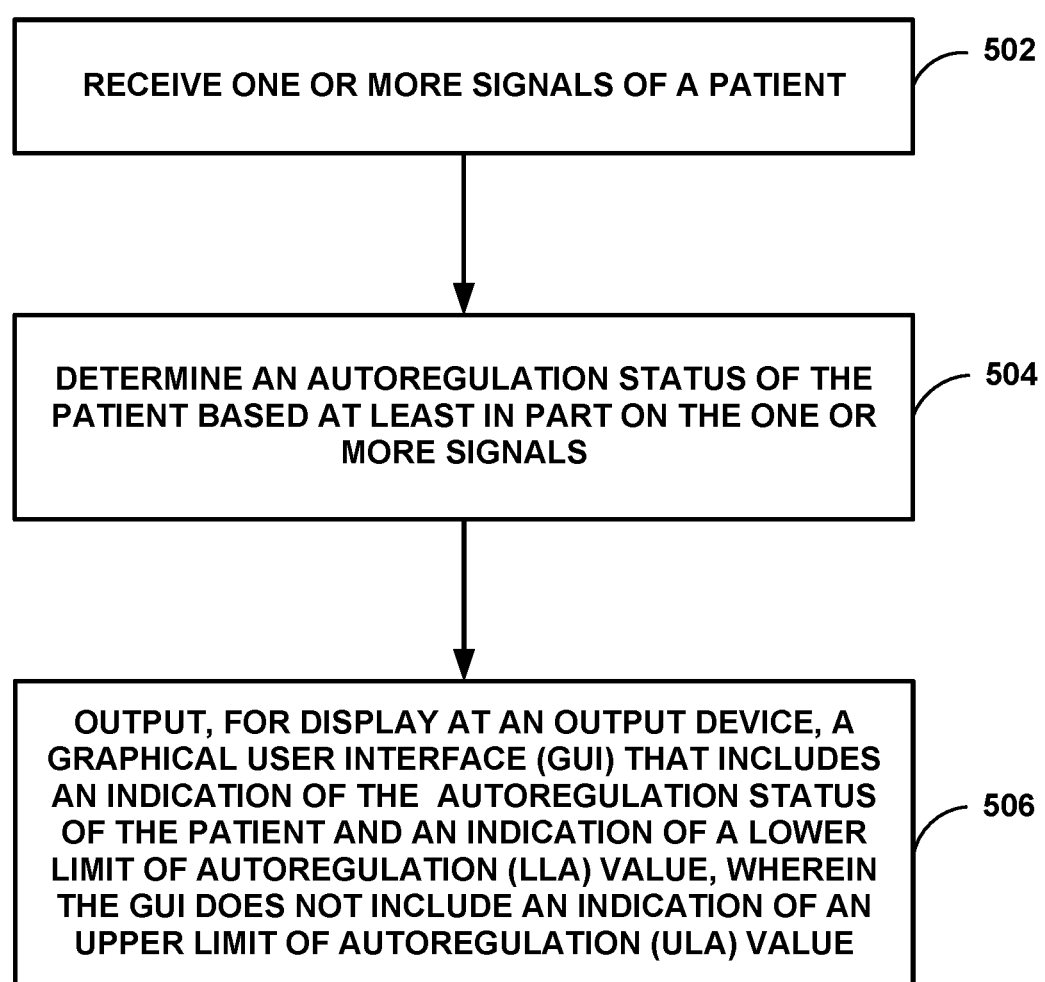

RECEIVE ONE OR MORE SIGNALS OF A PATIENT — 502

DETERMINE AN AUTOREGULATION STATUS OF THE PATIENT BASED AT LEAST IN PART ON THE ONE OR MORE SIGNALS — 504

OUTPUT, FOR DISPLAY AT AN OUTPUT DEVICE, A GRAPHICAL USER INTERFACE (GUI) THAT INCLUDES AN INDICATION OF THE AUTOREGULATION STATUS OF THE PATIENT AND AN INDICATION OF A LOWER LIMIT OF AUTOREGULATION (LLA) VALUE, WHEREIN THE GUI DOES NOT INCLUDE AN INDICATION OF AN UPPER LIMIT OF AUTOREGULATION (ULA) VALUE — 506

FIG. 5

AUTOREGULATION STATUS MONITORING

This application is a continuation-in-part of U.S. patent application Ser. No. 16/204,061 entitled, "COMPENSATION FOR BLOOD PRESSURE SENSOR MOVEMENT" and filed on Nov. 29, 2018, the entire content of which is incorporated herein by reference.

TECHNICAL FIELD

This disclosure relates to monitoring autoregulation status of a patient.

BACKGROUND

Clinicians may monitor one or more physiological parameters of a patient, e.g., to monitor a patient's autoregulation status. Autoregulation is the response mechanism by which an organism regulates blood flow over a wide range of systemic blood pressure changes through complex myogenic, neurogenic, and metabolic mechanisms. During autoregulation, arterioles dilate or constrict in an attempt to maintain appropriate blood flow. Autoregulation may occur for a variety of organs and organ systems, such as, for example, the brain, the kidneys, the gastrointestinal tract, and the like. In the example of cerebral autoregulation, as cerebral blood pressure decreases, cerebral arterioles dilate in an attempt to maintain blood flow. As cerebral pressure increases, cerebral arterioles constrict to reduce the blood flow that could cause injury to the brain.

SUMMARY

This disclosure describes devices, systems, and techniques for monitoring a patient's autoregulation status by outputting, for display at a display device, a graphical user interface (GUI) that indicates the autoregulation (e.g., cerebral and/or non-cerebral) status value of a patient. When the patient exhibits an impaired autoregulation status, the patient may experience inappropriate blood flow, which may be undesirable. An autoregulation system of the patient may be impaired if the blood pressure gradient and the oxygen saturation gradient trend together (e.g., change in the same direction) over a period of time. An intact autoregulation status of the patient occurs over a range of blood pressures defined between a lower limit of autoregulation (LLA) and an upper limit of autoregulation (ULA). For example, below a lower limit of autoregulation (LLA), a drop in blood flow to a respective organ may cause ischemia and adversely affect the respective organ. A clinician may use the GUI to monitor the autoregulation status of a patient, e.g., during a medical procedure, and take one or more actions to keep the patient in or bring the patient to an intact autoregulation status, such as by increasing or decreasing the patient's blood pressure.

While an indication of the LLA may be useful to clinicians monitoring the autoregulation status of the patient to determine whether the patient is in an intact autoregulation state or in an impaired autoregulation state by watching whether the blood pressure value of the patient, the ULA may not provide much useful information to the clinician. In fact, the ULA may distract clinicians from monitoring whether the patient is in an intact autoregulation state or in an impaired autoregulation state.

As such, in accordance with aspects of the present disclosure, a monitoring device, such as a regional oximetry device, may output, for display at a display device, a GUI for monitoring the autoregulation status of the patient that does not include an indication of the ULA. Instead, the GUI may include information such as the blood pressure values of the patient over time, the autoregulation status of the patient over time, and the LLA (e.g., a patient-specific LLA).

By not including an indication of the ULA in the GUI, the techniques of this disclosure may provide a GUI for monitoring the autoregulation status of a patient that is easier to use and less distracting to the clinician. For example, the GUI may be less cluttered with information because the GUI does not include an indication of the ULA, thereby allowing clinicians to focus on the LLA of the patient. Making the GUI that is easier to use and less distracting for the clinician may lead to better medical outcomes for the patient.

In some aspects, a method includes receiving, by processing circuitry, one or more signals of a patient; determining, by the processing circuitry, an autoregulation status of the patient based at least in part on the one or more signals; and outputting, by the processing circuitry and for display at an output device, a graphical user interface (GUI) that includes an indication of the autoregulation status of the patient and an indication of a lower limit of autoregulation (LLA) value, wherein the GUI does not include an indication of an upper limit of autoregulation (ULA) value.

In some aspects, a system includes one or more sensing devices; and processing circuitry configured to: receive, from the one or more sensing devices, one or more signals of a patient; determine an autoregulation status of the patient based at least in part on the one or more signals; and output, for display at an output device, a graphical user interface (GUI) that includes an indication of the autoregulation status of the patient and an indication of a lower limit of autoregulation (LLA) value, wherein the GUI does not include an indication of an upper limit of autoregulation (ULA) value.

In some aspects, a non-transitory computer readable storable medium comprising instructions that, when executed, cause processing circuitry to: receive one or more signals of a patient; determine an autoregulation status of the patient based at least in part on the one or more signals; and output, for display at an output device, a graphical user interface (GUI) that includes an indication of the autoregulation status of the patient and an indication of a lower limit of autoregulation (LLA) value, wherein the GUI does not include an indication of an upper limit of autoregulation (ULA) value.

The details of one or more examples are set forth in the accompanying drawings and the description below. Other features, objects, and advantages will be apparent from the description and drawings, and from the claims.

BRIEF DESCRIPTION OF DRAWINGS

FIG. 5 is a flow diagram illustrating an example technique for presenting the autoregulation status of a patient.

DETAILED DESCRIPTION

Figure 1:
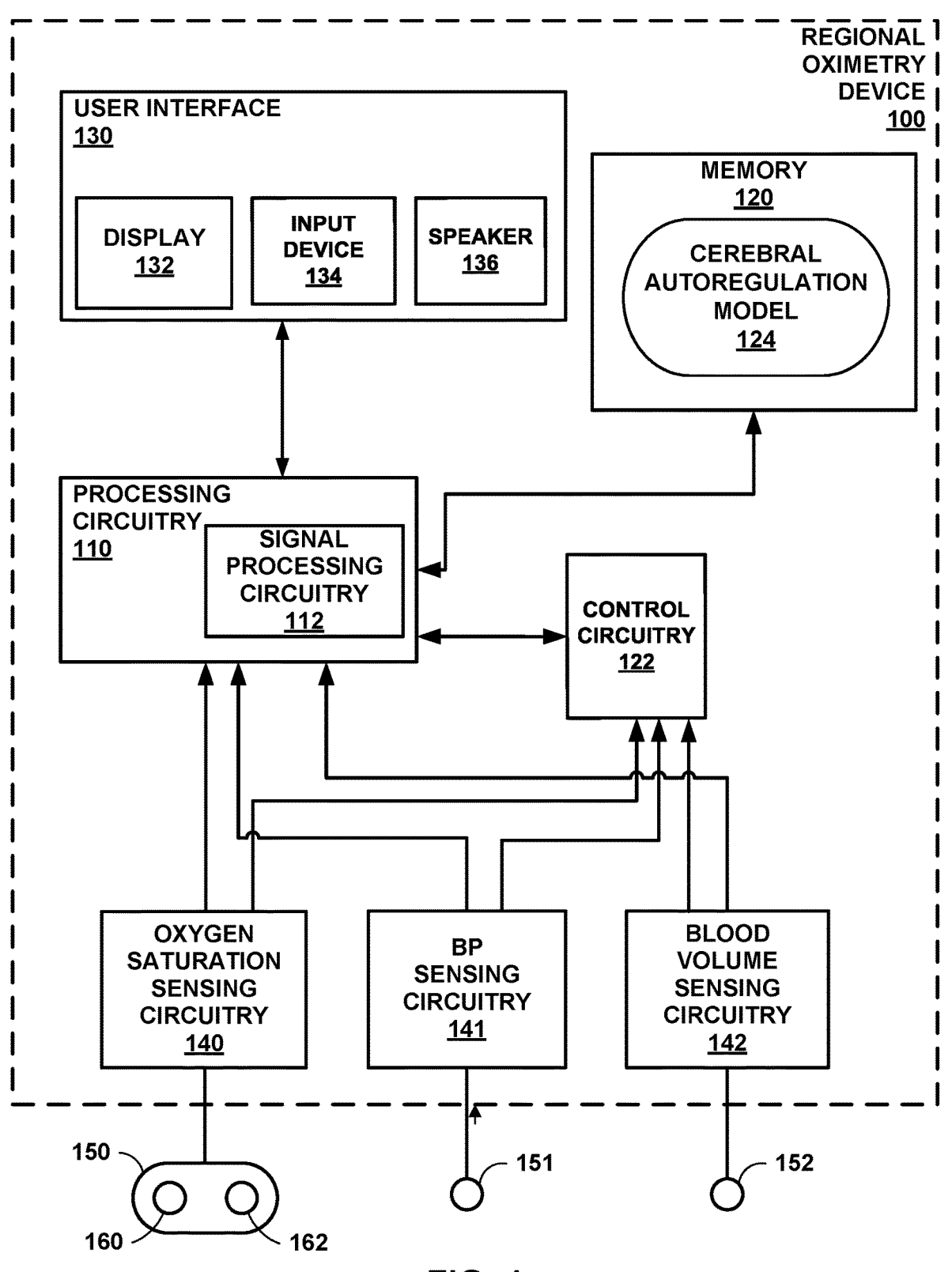
FIG. 1 is a conceptual block diagram illustrating an example regional oximetry device.

FIG. 1 is a conceptual block diagram illustrating an example regional oximetry device 100. Regional oximetry device 100 includes processing circuitry 110, memory 120, control circuitry 122, user interface 130, sensing circuitry 140, 141, and 142, and sensing device(s) 150, 151, and 152. In the example shown in FIG. 1, user interface 130 may include display 132, input device 134, and/or speaker 136, which may be any suitable audio device configured to generate and output a noise and include any suitable circuitry. In some examples, regional oximetry device 100 may be configured to determine and output (e.g., for display at display 132) the autoregulation status of a patient, e.g., during a medical procedure or for more long-term monitoring, such as in the intensive care unit (ICU) or for fetal monitoring of prenatal infants, children, or adults. A clinician may receive information regarding the autoregulation status of a patient via user interface (e.g., at display 132) and adjust treatment or therapy to the patient based on the autoregulation status information. Although regional oximetry device 100 is described as an example device herein, other devices may calculate blood pressure and/or use blood pressure for other physiological monitoring and perform similar a compensation process on blood pressures subjected to abrupt changes in the measured blood pressure values.

Processing circuitry 110 as well as other processors, processing circuitry, controllers, control circuitry, and the like, described herein, may include one or more processors. Processing circuitry 110 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 110 may include multiple components, such as any combination of one or more microprocessors, one or more DSPs, one or more ASICs, or one or more FPGAs, as well as other discrete or integrated logic circuitry, and/or analog circuitry.

Control circuitry 122 may be operatively coupled processing circuitry 110. Control circuitry 122 is configured to control an operation of sensing devices 150-152. In some examples, control circuitry 122 may be configured to provide timing control signals to coordinate operation of sensing devices 150-152. For example, sensing circuitry 140-142 may receive from control circuitry 122 one or more timing control signals, which may be used by sensing circuitry 140-142 to turn on and off respective sensing devices 150-152, such as to periodically collect calibration data using sensing devices 150-152. In some examples, processing circuitry 110 may use the timing control signals to operate synchronously with sensing circuitry 140-142. For example, processing circuitry 110 may synchronize the operation of an analog-to-digital converter and a demultiplexer within sensing circuitry 140-142 based on the timing control signals.

Memory 120 may be configured to store measurements of blood pressure, oxygen saturation, blood volume, other physiological parameters, relationships between blood pressure and physiological parameters, MAP values, rSO$_2$ values, COx values, BVS values, HVx values, and/or value(s) of an LLA and/or a ULA, for example. Memory 120 may also be configured to store data such as thresholds for detecting abrupt changes in blood pressure, previous LLA and ULA values, and/or other physiological parameters and expected values of physiological parameters. Memory 120 may also be configured to store data such as threshold levels for physiological parameters, threshold values for blood pressure, and/or threshold levels for signal quality metrics.

Memory 120 may also be configured to store autoregulation state values including modified and unmodified values, threshold values and rates, smoothing functions, Gaussian filters, confidence metrics, expected autoregulation functions, historical patient blood pressure value data, and/or estimates of limits of autoregulation. The threshold values and rates, smoothing functions, Gaussian filters, confidence metrics, expected autoregulation functions, and historical patient blood pressure value may stay constant throughout the use of device 100 and across multiple patients, or these values may change over time.

In some examples, memory 120 may store program instructions, such as one or more neural network algorithms. The program instructions may also include one or more program modules that are executable by processing circuitry 110. For example, memory 120 may store an autoregulation model, which may be a model trained via machine learning to determine the autoregulation status of a patient. When executed by processing circuitry 110, such program instructions, such as program instructions of the autoregulation model, may cause processing circuitry 110 to provide the functionality ascribed to it herein. In some examples, memory 120 may store instructions regarding how to determine abrupt changes in measured blood pressure, calculating ULA and LLA values, and presenting information to the user via user interface 130. The program instructions may be embodied in software, firmware, and/or RAMware. Memory 120, as well as other memory devices described herein (e.g., memory 220 shown in FIG. 2), may include any volatile, non-volatile, magnetic, optical, circuitry, or electrical media, such as a random access memory (RAM), read-only memory (ROM), non-volatile RAM (NVRAM), electrically-erasable programmable ROM (EEPROM), flash memory, or any other digital media.

User interface 130 and/or display 132 may be configured to present information to a user (e.g., a clinician). User interface 130 and/or display 132 may be configured to present a graphical user interface to a user, where each graphical user interface may include indications of values of one or more physiological parameters of a patient. For example, processing circuitry 110 may be configured to present autoregulation state values, blood pressure values, physiological parameter values (e.g., heart rate), and indications of autoregulation status (e.g., cerebral autoregulation status) of a patient via display 132. While processing circuitry 110 may be configured to present the LLA of the patient at user interface 130 and/or display 132, processing circuitry 110 may refrain from presenting the ULA of the patient at user interface 130 and/or display 132. In examples in which processing circuitry 110 determines that the autoregulation status of the patient is impaired, then processing circuitry 110 may present a notification (e.g., an alert) indicating the impaired autoregulation status via display 132. As another example, processing circuitry 110 may present, via display 132, estimates of regional oxygen saturation (rSO$_2$) for a patient, an estimate of the blood oxygen saturation (SpO$_2$) determined by processing circuitry 110, pulse rate information, respiration rate information, blood pressure, any other patient parameters, or any combination thereof.

User interface 130 and/or display 132 may include a monitor, cathode ray tube display, a flat panel display such as a liquid crystal (LCD) display, a plasma display, a light emitting diode (LED) display, and/or any other suitable display. User interface 130 and/or display 132 may be part of a personal digital assistant, mobile phone, tablet computer, laptop computer, any other suitable computing device, or any combination thereof, with a built-in display or a separate display. User interface 130 may also include means for projecting audio to a user, such as speaker(s). Processing circuitry 110 may be configured to present, via user interface 130, a visual, audible, tactile, or somatosensory notification (e.g., an alarm signal) indicative of the patient's autoregulation status and/or a notification indicative of the patient's limit(s) of autoregulation. User interface 130 may include or be part of any suitable device for conveying such information, including a computer workstation, a server, a desktop, a notebook, a laptop, a handheld computer, a mobile device, or the like. In some examples, processing circuitry 110 and user interface 130 may be part of the same device or supported within one housing (e.g., a computer or monitor). In other examples, processing circuitry 110 and user interface 130 may be separate devices configured to communicate through a wired connection or a wireless connection (e.g., communication interface 290 shown in FIG. 2).

In some examples, processing circuitry 110 may be configured to present, by user interface 130, such as display 132, a graphical user interface to a user. The graphical user interface may include indications of values of one or more physiological parameters of a patient, such as, for example, blood pressure values, oxygen saturation values, information about an autoregulation status (e.g., cerebral autoregulation status values and/or non-cerebral autoregulation status values), the LLA of the patient, pulse rate information, respiration rate information, other patient physiological parameters, or combinations thereof via display 132. User interface 130 may also include circuitry and other components configured to generate and project an audio output to a user, such as speaker 136.

In some examples, processing circuitry 110 may also receive input signals from additional sources (not shown), such as a user. For example, processing circuitry 110 may receive from input device 134, such as a keyboard, a mouse, a touch screen, buttons, switches, a microphone, a joystick, a touch pad, or any other suitable input device or combination of input devices, an input signal. The input signal may contain information about the patient, such as physiological parameters, treatments provided to the patient, or the like. Additional input signals may be used by processing circuitry 110 in any of the determinations or operations it performs in accordance with processing circuitry 110.

In some examples, if processing circuitry 110 determines that the autoregulation status of the patient is impaired, then processing circuitry 110 may present a notification indicating the impairment. The notification may include a visual, audible, tactile, or somatosensory notification (e.g., an alarm signal) indicative of the autoregulation status of the patient.

Sensing circuitry 140, 141, and 142 may be configured to receive physiological signals sensed by respective sensing device(s) 150, 151, and 152 and communicate the physiological signals to processing circuitry 110. Sensing device(s) 150, 151, and 152 may include any sensing hardware configured to sense a physiological parameter of a patient, such as, but not limited to, one or more electrodes, optical receivers, blood pressure cuffs, or the like. Sensing circuitry 140, 141, and 142 may convert the physiological signals to usable signals for processing circuitry 110, such that processing circuitry 110 is configured to receive signals generated by sensing circuitry 140, 141, and 142. Sensing circuitry 140, 141, and 142 may receive signals indicating physiological parameters from a patient, such as, but not limited to, blood pressure, regional oxygen saturation, blood volume, heart rate, and respiration. Sensing circuitry 140, 141, and 142 may include, but are not limited to, blood pressure sensing circuitry, oxygen saturation sensing circuitry, regional oxygen saturation sensing circuitry, regional oxygen saturation sensing circuitry, blood volume sensing circuitry, heart rate sensing circuitry, temperature sensing circuitry, electrocardiography (ECG) sensing circuitry, electroencephalogram (EEG) sensing circuitry, or any combination thereof. In some examples, sensing circuitry 140, 141, and 142 and/or processing circuitry 110 may include signal processing circuitry such as an analog-to-digital converter.

In some examples, sensing circuitry 140-142 and/or processing circuitry 110 may include signal processing circuitry 112 configured to perform any suitable analog conditioning of the sensed physiological signals. For example, sensing circuitry 140-142 may communicate to processing circuitry 110 an unaltered (e.g., raw) signal. Processing circuitry 110, e.g., signal processing circuitry 112, may be configured to modify a raw signal to a usable signal by, for example, filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof. In some examples, the conditioned analog signals may be processed by an analog-to-digital converter of signal processing circuitry 112 to convert the conditioned analog signals into digital signals. In some examples, signal processing circuitry 112 may operate on the analog or digital form of the signals to separate out different components of the signals. In some examples, signal processing circuitry 112 may perform any suitable digital conditioning of the converted digital signals, such as low pass, high pass, band pass, notch, averaging, or any other suitable filtering, amplifying, performing an operation on the signal, performing any other suitable digital conditioning, or any combination thereof. In some examples, signal processing circuitry 112 may decrease the number of samples in the digital detector signals. In some examples, signal processing circuitry 112 may remove dark or ambient contributions to the received signal. Additionally or alternatively, sensing circuitry 140-142 may include signal processing circuitry 112 to modify one or more raw signals and communicate to processing circuitry 110 one or more modified signals.

In some examples, oxygen saturation sensing device 150 is a regional oxygen saturation sensor configured to generate an oxygen saturation signal indicative of blood oxygen saturation within the venous, arterial, and/or capillary systems within a region of the patient. For example, oxygen saturation sensing device 150 may be configured to be placed on the patient's skin, such as on the patient's forehead, and may be used to determine the regional oxygen saturation of a particular tissue region (e.g., in the frontal cortex or another cerebral location).

In such cases, oxygen saturation sensing device 150 may include emitter 160 and detector 162. Emitter 160 may include at least two light emitting diodes (LEDs), each configured to emit at different wavelengths of light, e.g., red or near infrared light. As used herein, the term "light" may refer to energy produced by radiative sources and may include any wavelength within one or more of the ultrasound, radio, microwave, millimeter wave, infrared, visible, ultraviolet, gamma ray or X-ray electromagnetic radiation spectra. In some examples, light drive circuitry (e.g., within sensing device 150, sensing circuitry 140, control circuitry 122, and/or processing circuitry 110) may provide a light drive signal to drive emitter 160 and to cause emitter 160 to emit light. In some examples, the LEDs of emitter 160 emit light in the wavelength range of about 600 nanometers (nm) to about 1000 nm. In a particular example, one LED of emitter 160 is configured to emit light at a wavelength of about 730 nm and the other LED of emitter 160 is configured to emit light at a wavelength of about 810 nm. Other wavelengths of light may also be used in other examples.

Detector 162 may include a first detection element positioned relatively "close" (e.g., proximal) to emitter 160 and a second detection element positioned relatively "far" (e.g., distal) from emitter 160. In some examples, the first detection elements and the second detection elements may be chosen to be specifically sensitive to the chosen targeted energy spectrum of light source 160. Light intensity of multiple wavelengths may be received at both the "close" and the "far" detector 162. For example, if two wavelengths are used, the two wavelengths may be contrasted at each location and the resulting signals may be contrasted to arrive at a regional oxygen saturation value that pertains to additional tissue through which the light received at the "far" detector passed (tissue in addition to the tissue through which the light received by the "close" detector passed, e.g., the brain tissue), when it was transmitted through a region of a patient (e.g., a patient's cranium). Surface data from the skin and skull may be subtracted out, to generate a regional oxygen saturation signal for the target tissues over time.

Oxygen saturation sensing device 150 may provide the regional oxygen saturation signal (e.g., regional oxygen saturation signal) to processing circuitry 110 or to any other suitable processing device to enable evaluation of an autoregulation status of the patient. Additional example details of determining oxygen saturation based on light signals may be found in commonly assigned U.S. Pat. No. 9,861,317, which issued on Jan. 9, 2018, and is entitled "Methods and Systems for Determining Regional Blood Oxygen Saturation."

In operation, blood pressure sensing device 151 and oxygen saturation sensing device 150 may each be placed on the same or different parts of the patient's body. For example, blood pressure sensing device 151 and oxygen saturation sensing device 150 may be physically separate from each other and may be separately placed on the patient. As another example, blood pressure sensing device 151 and oxygen saturation sensing device 150 may in some cases be part of the same sensor or supported by a single sensor housing. For example, blood pressure sensing device 151 and oxygen saturation sensing device 150 may be part of an integrated oximetry system configured to non-invasively measure blood pressure (e.g., based on time delays in a PPG signal) and regional oxygen saturation.

One or both of blood pressure sensing device 151 or oxygen saturation sensing device 150 may be further configured to measure other parameters, such as hemoglobin, respiratory rate, respiratory effort, heart rate, saturation pattern detection, response to stimulus such as bispectral index (BIS) or electromyography (EMG) response to electrical stimulus, or the like. While an example regional oximetry device 100 is shown in FIG. 1, the components illustrated in FIG. 1 are not intended to be limiting. Additional or alternative components and/or implementations may be used in other examples.

Blood pressure sensing device 151 may be any sensor or device configured to obtain the patient's blood pressure (e.g., arterial blood pressure). In one example, the blood pressure sensing device 151 may include or be connected to a probe configured to be inserted into a blood pressure of the patient. In another example, blood pressure sensing device 151 may include a blood pressure cuff for non-invasively monitoring blood pressure, a sensor configured to non-invasively generate a PPG signal, or an arterial line for invasively monitoring blood pressure (e.g., a pressure probe configured to be placed within an artery or vein). In some examples, the blood pressure signal may include at least a portion of a waveform of the acquisition blood pressure. In some examples, an acquisition site may include at least one of a femoral artery of the patient, a radial artery of the patient, a dorsalis pedis artery of the patient, a brachial artery of the patient, or combinations thereof. In certain examples, blood pressure sensing device 151 may include one or more pulse oximetry sensors.

In some examples, blood pressure sensing device 151 may include a plurality of blood pressure sensing devices. For example, each blood pressure sensing device of the plurality of blood pressure sensing devices may be configured to obtain a respective blood pressure of the patient at a respective acquisition site of a plurality of acquisition sites. The plurality of acquisition sites may include similar or different arteries of the patient. In some such cases, the patient's blood pressure may be derived by processing time delays between two or more characteristic points within a single plethysmography (PPG) signal obtained from a single pulse oximetry sensor.

Additional example details of deriving blood pressure based on a comparison of time delays between certain components of a single PPG signal obtained from a single pulse oximetry sensor are described in commonly assigned U.S. Patent Application Publication No. 2009/0326386 filed Sep. 30, 2008, and entitled "Systems and Methods for Non-Invasive Blood Pressure Monitoring," the entire content of which is incorporated herein by reference. In other cases, the patient's blood pressure may be continuously, non-invasively monitored via multiple pulse oximetry sensors placed at multiple locations on the patient's body. As described in commonly assigned U.S. Pat. No. 6,599,251, issued Jul. 29, 2003, entitled "Continuous Non-invasive Blood Pressure Monitoring Method and Apparatus," the entire content of which is incorporated herein by reference, multiple PPG signals may be obtained from the multiple pulse oximetry sensors, and the PPG signals may be compared against one another to estimate the patient's blood pressure.

Regardless of its form, blood pressure sensing device 151 may be configured to generate a blood pressure signal indicative of the patient's blood pressure (e.g., arterial blood pressure) over time. In examples in which blood pressure sensing device 151 includes a plurality of blood pressure sensing devices, the blood pressure signal may include a plurality of blood pressure signals, each indicative of a blood pressure of the patient at a respective acquisition site. Blood pressure sensing device 151 may provide the blood pressure signal to sensing circuitry 141, processing circuitry 110, or to any other suitable processing device to enable evaluation of the patient's autoregulation status.

Processing circuitry 110 may be configured to receive one or more signals generated by sensing devices 150, 151, and 152 and sensing circuitry 140, 141, and 142. The signals may include a signal indicating blood pressure, a signal indicating oxygen saturation, and/or a signal indicating blood volume of a patient. Processing circuitry 110 may be configured to determine values of physiological parameters of the patient based on two or more signals received by sensing devices 150-152 and sensing circuitry 140-142 and delivered to processing circuitry 110. Sensing devices 150-152 and sensing circuitry 140-142 can deliver the signals directly to processing circuitry 110 or sensing circuitry 140-142 can modify the signals (e.g., through pre-processing) before delivering signals to processing circuitry 110. In some examples, processing circuitry 110 may be configured to determine a relationship between blood pressure values of the patient and a physiological parameter of the patient, such as a correlation index (e.g., COx, a hemoglobin volume index (HVx)), an oxygen saturation value, a blood volume value (e.g., an isosbestic signal), a gradient-based metric of two or more physiological parameters, and/or another physiological parameter.

Processing circuitry 110 may be configured to determine the autoregulation status of a patient based on any combination of the signals received by sensing devices 150-152 and/or generated by sensing circuitry 140-142 and using any suitable technique. For example, processing circuitry 110 can determine a gradients-based metric by determining respective gradients of signals for physiological parameters and determining whether the respective gradients trend together. These gradients may be used in a technique to indicate the autoregulation status of a patient as described in, for example, U.S. Patent Application No. 2018/0014791 by Montgomery et al., entitled "SYSTEMS AND METHODS OF MONITORING AUTOREGULATION," and filed on Jul. 13, 2017, which is incorporated herein by reference in its entirety.

In some examples, processing circuitry 110 may be configured to determine the blood pressure values for which the physiological parameter is less than or greater than one or more threshold values. As an example, processing circuitry 110 may determine an estimate of the lower limit of autoregulation (LLA) based on the lowest blood pressure value at which the expected value of COx is less than a threshold value, such as 0.5, 0.4, 0.3, 0.2, 0.1, or 0.0 (e.g., wherein 1.0 represents full correlation and 0.0 represents no correlation between blood pressure and $rSO_2$). Thus, processing circuitry 110 may determine estimates of the limits of autoregulation (e.g., the LLA and the upper limit of autoregulation (ULA)) based on the blood pressure and $rSO_2$. Additional example details of determining LLA and/or ULA and autoregulation status may be found in commonly assigned U.S. Patent Application Publication No. 2018/0014791 filed on Jul. 13, 2017, and entitled "Systems and Methods of Monitoring Autoregulation," and commonly assigned U.S. Provisional Patent Application No. 62/510,303 filed on May 24, 2017, and entitled "Determining a Limit of Autoregulation," the entire contents of each of which are incorporated herein by reference.

Processing circuitry 110 may be configured to determine that the patient has an intact autoregulation based on determining that a most recent blood pressure value of the patient is between the upper and lower limits of autoregulation. In addition, the LLA and ULA may be continually calculated and updated based on newly measured blood pressure values and COx values. Since abrupt changes in the measured blood pressure from issues with measurement hardware (e.g., pressure probe location or pressure cuff deformation) will be used by processing circuitry 110 to determine the blood pressure, LLA, ULA, and overall autoregulation status, the processes described herein for compensating or mitigating errors in blood pressure measurement may enable more accurate monitoring of the patient despite these issues with blood pressure measurement.

For example, a device such as regional oximetry device 100 may include memory circuitry (e.g., memory 120) configured to store a first blood pressure value representative of a blood pressure of a patient sensed by a blood pressure sensor at a first time. Device 100 may also include processing circuitry (e.g., processing circuitry 110) that is configured to receive a second blood pressure value representative of the blood pressure of the patient sensed by the blood pressure sensor at a second time (after the first time) and determine a difference value between the first blood pressure value and the second blood pressure value. The difference value may be an absolute magnitude of blood pressure (e.g., 10 mmHg) or a rate of change of blood pressure (e.g., 30 mmHg per second). Processing circuitry 110 may then determine that the difference value is greater than or equal to a threshold value. The threshold value may be a blood pressure value (e.g., 10 mmHg), a rate of change in blood pressure, blood pressure value change between a certain number of blood pressure measurement samples, or any other type of threshold. In the case of a rate of change, the difference value may be a difference rate of change of the difference value over a period of time between the first time and the second time, wherein the threshold comprises a threshold rate of change. In other examples, the threshold value may be a formula or other complex threshold that incorporates values such as the measured blood pressure change and/or a rate of change in the blood pressure (e.g., a blood pressure change may be determined to be abrupt when both the magnitude of the difference and the rate of change exceeds respective thresholds).

In some examples, in response to determining that the difference value is greater than or equal to the threshold value, processing circuitry 110 may generate an offset value that compensates for the difference value between the first blood pressure value and the second blood pressure. The offset value may be an additive inverse of the difference value (or of the magnitude of the change in blood pressure corresponding to a supra-threshold rate of change in blood pressure). For example, the offset value may be −10 mmHg if the measured blood pressure had an identified increase in blood pressure of 10 mmHg. In other examples, the offset value may differ from the additive inverse of the difference value.

Processing circuitry 110 may then generate at least one updated parameter value. The at least one updated parameter value may be determined based on the offset value and subsequently received blood pressure values representative of the blood pressure of the patient sensed after the second time. Since the blood pressures sensed after the second time will have been affected by the abrupt change in measured blood pressure, the offset value may be used to "correct" or otherwise compensate for the difference value reflected in these affected measured blood pressures. For example, the updated parameter value may be an updated blood pressure value for which the offset value is directly added to the measured blood pressure values. As another example, processing circuitry 110 may determine another updated parameter value, such as an updated LLA value or updated ULA value by adding the offset value to the previously calculated LLA or ULA values to essentially adjust the LLA or ULA threshold to the affected blood pressure values. In this manner, processing circuitry 110 may still identify intact or impaired autoregulation for the patient using previously determined LLA and ULA values even though the measured blood pressure values may have changed. Processing circuitry 110 may then output the at least one updated parameter value. For example, processing circuitry 110 may transmit the at least one updated parameter values to another device for monitoring or other calculations, or processing circuitry 110 may control a display device to display a representation of the updated parameter values.

As discussed above, in one example, the updated parameter value may be an updated blood pressure value. Processing circuitry 110 may be configured to generate the updated blood pressure values by at least applying the offset value to the second blood pressure value and the subsequently received blood pressure values representative of the blood pressure of the patient sensed after the second time. In other words, the offset value may be applied to the affected blood pressure values measured after the detected abrupt change in blood pressure values.

Alternatively, or additionally, the updated parameter value may be at least one of an updated LLA value or an updated ULA value. Processing circuitry 110 may be configured to generate at least one of the updated LLA value or the updated ULA value by at least applying the offset value to at least one of a determined LLA value or a determined ULA value based on the subsequently received blood pressure values representative of the blood pressure of the patient sensed after the second time. For example, if the measured blood pressure values have increased due to movement of the pressure probe, then the LLA and ULA previously used to monitor autoregulation of a patient may no longer be accurate. However, applying the offset value to the LLA and ULA values calculated based on the new, higher, blood pressure values may maintain help the validity of the LLA and ULA thresholds for determining the autoregulation status of the patient. In one example, processing circuitry 110 may be configured to control a display device to display at least one of the updated LLA value or the updated ULA value moving forward after the abrupt change in blood pressure and display at least one of a prior LLA value or a prior ULA value generated based on blood pressure values representative of blood pressure sensed prior to the second time. In this manner, the LLA and ULA values displayed on the screen will be different before and after the point in time that the abrupt change in measured blood pressure occurred.

In some examples in which processing circuitry 110 does not apply the offset value to blood pressure values measured after the detected abrupt change, processing circuitry 110 may determine the updated LLA values and updated ULA values based on the unchanged measured blood pressure values and downweighted blood pressure values representative of the blood pressure sensed prior to the second time. In other words, processing circuitry 110 may determine LLA and ULA values multiple blood pressure values sensed over time. After processing circuitry 110 identifies an abrupt change in measured blood pressure (e.g., a change in measured blood pressure that is identified as associated with probe movement instead of physiological changes), the previously measured blood pressure values are less relevant to updated LLA values and updated ULA values calculated using the offset value. Therefore, processing circuitry 110 may reduce the weighting of the prior blood pressure values to reduce the impact of these pre-abrupt change blood pressure values from affecting the updated LLA values and updated ULA values.

In some examples, the pressure probe of blood pressure sensor 151 that can be placed within the blood vessel may include an accelerometer or other movement sensor configured to generate a signal (referred to herein as a movement signal) indicative of movement of the pressure probe within the blood vessel. In these examples, processing circuitry 110 may be configured to receive a movement signal from blood pressure sensor 151 representative of movement of a probe of blood pressure sensor 151, which may indicate movement of the probe with respect to the blood vessel within which the probe is disposed. Processing circuitry 110 may compare a characteristic of the movement signal to a movement threshold and determine that the movement signal is greater than or equal to the movement threshold. The characteristic can include, for example, a discrete amplitude, a peak, mean, or lowest amplitude for a predetermined range of time, a frequency of the signal, a frequency band (e.g., fundamental frequency) component of the signal, or the like.

In response to determining that the characteristic of the movement signal is greater than or equal to the movement threshold and the difference value calculated for the change in the blood pressure is greater than or equal to the threshold value, processing circuitry 110 may generate the offset value that compensates for the difference value determined between the first blood pressure value and the second blood pressure. In this manner, the movement signal may help processing circuitry 110 distinguish between abrupt changes in blood pressure that may be physiological and those abrupt changes in blood pressure caused by movement of the pressure prove or other non-physiological cause of the change in blood pressure.

In some examples, device 100 may present via user interface 130 an indication that the pressure probe has moved or the displayed information related to blood pressure may be compromised due to an issue such as pressure probe movement. These indications may be in addition to, or instead of, adjusting a parameter value such as the blood pressure, LLA, or ULA based on an offset value. In other words, the presented indications that the pressure probe may have moved may indicate that the blood pressure measurements, or information based on the blood pressure measurements, may be inaccurate. For example, processing circuitry 110 may be configured to, in response to determining that the difference value is greater than or equal to the threshold value, control display 132 of user interface 130 to present a notification (e.g., a warning) that indicates autoregulation information determined based on blood pressure values received prior to the second time is inaccurate. This warning could be in the form of a visual indication (e.g., change of color of a visual indicia, text, arrows, etc.), audible alert, or tactile alert.

In other examples, processing circuitry 110 may be configured to, in response to determining that the second blood pressure is greater than or equal to the threshold value, control the user interface to display first autoregulation information (e.g., prior determined LLA and ULA values) generated based on blood pressure values representing the blood pressure sensed prior to the second time in greyscale (or other color) and also display second autoregulation information (e.g., updated LLA and ULA values) generated based on blood pressure values representing the blood pressure sensed after, and including, the second time in one or more colors different than the greyscale (or the other color). In this manner, the change in color of the displayed LLA and ULA values may indicate to the user which autoregulation information is currently relevant to the sensed blood pressure values. In other examples, processing circuitry 110 may be configured to, in response to determining that the second blood pressure exceeds the threshold value, control a user interface to present a warning that indicates a blood pressure anomaly due to movement of a probe of the blood pressure sensor within the patient. In some examples, this notification may reference a point in time at which the abrupt change in blood pressure occurred so that the user can quickly identify why the abrupt change in blood pressure may have occurred at that time.

In some examples, processing circuitry 110 may employ a process for analyzing the blood pressure signal (e.g., two or more blood pressure values that may be discrete or an analog signal) for characteristics indicative of pressure prove movement. For example, processing circuitry 110 may identify probe movement in response to detecting type of waveform shape, number of waves over a certain period of time, waveform frequency, spectral analysis of the waveform, or any other type of criteria. Processing circuitry 110 may employ such a process to differentiate probe movement or other sensor issues from physiological changes that may have manifested as the change to measured blood pressure.

In other examples, user interface 130 may receive user input from the clinician or other user indicating that pressure probe has moved within the patient or that some other sensor issue was identified. Processing circuitry 110 may compensate for any changes to the measured blood pressure in response to receiving this input. In some examples of receiving user input that the prove has been moved, processing circuitry 110 may even compensate for the changes to measured blood pressure that do not exceed the predetermined threshold. In other words, processing circuitry 110 may treat the user input as a command to reset the blood pressure values and/or LLA or ULA values. Similarly, processing circuitry 110 may be configured to receive user input that controls how processing circuitry 110 should compensate for an abrupt change in measured blood pressure. For example, processing circuitry 110 may receive user input that selects between adjusting the blood pressures (as shown in FIG. 5) and adjusting another parameter value (e.g., LLA and ULA as shown in FIG. 7).

The measured blood pressure values described herein may be rate blood pressure values indicative of the exact blood pressure at any given time (e.g., blood pressure values that indicate the blood pressure changes within a cardiac cycle). In other examples, the measured blood pressure values may refer to an average blood pressure, such as a mean arterial pressure (MAP) in which discrete blood pressure measurements have been taken and used to calculate an average pressure that does not identify intra-cardiac cycle blood pressure variations.

In some examples, processing circuitry 110 may be configured to determine a set of correlation coefficient values for the values of the first and second physiological parameters, which may include blood pressure values, oxygen saturation values, and/or blood volume values. Processing circuitry 110 may associate each correlation coefficient value with a blood pressure value. Based on the correlation coefficient value(s) associated with a particular blood pressure value (and, in some examples, nearby blood pressure values), processing circuitry 110 may be configured to determine an autoregulation state value associated with the particular blood pressure value. These techniques for determining an autoregulation state value associated with the particular blood pressure are described in, for example, U.S. Patent Application 2020/0187866 by Antunes, et al., entitled "BLOOD PRESSURE AND AUTOREGULATION MONITORING," and filed on Dec. 12, 2018 and U.S. Patent Application No. 2020/0129076 by Montgomery et al., entitled "IDENTIFYING ANOMALOUS AUTOREGULATION STATE VALUES," and filed on Oct. 24, 2018, which is incorporated herein by reference in its entirety.

In some examples, processing circuitry 110 may be configured to determine, using an autoregulation model, an autoregulation status of the patient based at least in part on the blood pressure of the patient during the period of time and the regional oxygen saturation of the patient during the period of time. The autoregulation model may include a neural network algorithm trained via machine learning to determine the autoregulation status of the patient based on a patient-specific LLA. Processing circuitry 110 may execute the autoregulation model and may use the MAP of the patient during the period of time and the regional oxygen saturation of the patient during the period of time as inputs to the autoregulation model to generate an output from the autoregulation model that is indicative of the autoregulation status of the patient.

Once processing circuitry 110 has determined the autoregulation status of the patient, processing circuitry 110 may generate and output information indicative of the autoregulation status of the patient to an output device, e.g., user interface 130. Processing circuitry 110 delivers the information to user interface 130. In some examples, the information may enable user interface 130, for example, display 132, speaker 136, and/or separate display(s) (not shown), to present a graphical user interface that includes information indicative of the autoregulation status of the patient, such as an autoregulation status value and/or an indication of an impaired autoregulation state of the brain. In some examples, the indication of autoregulation status may include text, colors, and/or audio presented to a user. Processing circuitry 110 may be further configured to present an indication of one or more autoregulation status values, the patient-specific LLA, blood pressure(s), oxygen saturation(s), or the like, on the graphical user interface. In addition to or instead of the graphical user interface, processor circuitry 110 may be configured to generate and present information indicative of a determined autoregulation status of the patient via speaker 136. For example, in response to detecting an impaired autoregulation state of the patient, processing circuitry 110 may generate an audible alert via speaker 136.

In some examples, device 100, e.g., processing circuitry 110 or user interface 130, may include a communication interface to enable device 100 to exchange information with external devices. The communication interface may include any suitable hardware, software, or both, which may allow device 100 to communicate with electronic circuitry, a device, a network, a server or other workstations, a display, or any combination thereof. For example, processing circuitry 110 may receive blood pressure values, oxygen saturation values, or predetermined data, such as predetermined cerebral autoregulation status values, predetermined non-cerebral autoregulation status value, or predetermined adjustment values from an external device via the communication interface.

The components of device 100 that are illustrated and described as separate components are illustrated and described as such for illustrative purposes only. In some examples the functionality of some of the components may be combined in a single component. For example, the functionality of processing circuitry 110 and control circuitry 122 may be combined in a single processor system. Additionally, in some examples the functionality of some of the components of device 100 illustrated and described herein may be divided over multiple components. For example, some or all of the functionality of control circuitry 122 may be performed in processing circuitry 110, or sensing circuitry 140-142 and 142. In other examples, the functionality of one or more of the components may be performed in a different order or may not be required.

Figure 2:
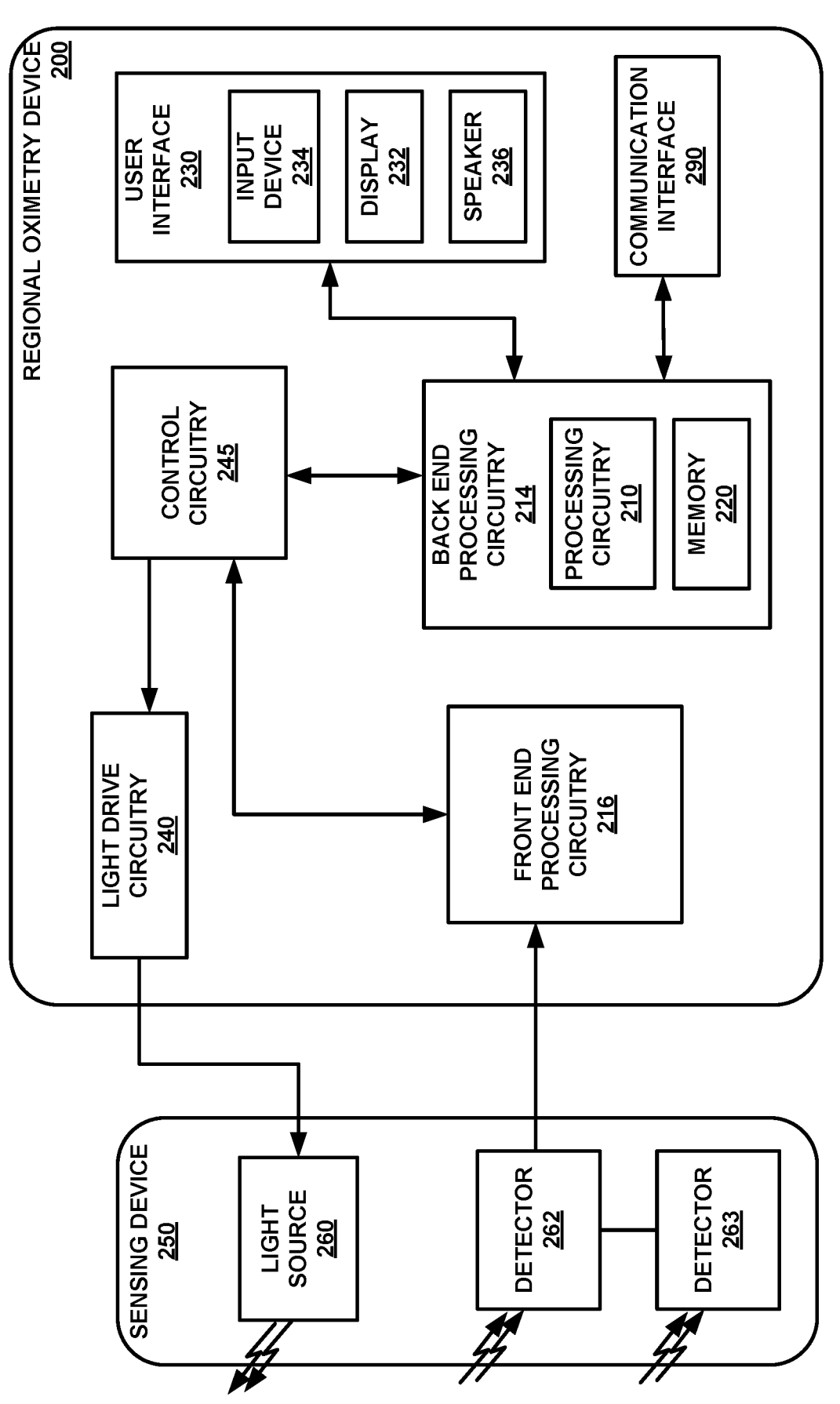
FIG. 2 is a conceptual block diagram illustrating an example regional oximetry device configured to monitor an autoregulation status of a patient.

FIG. 2 is a conceptual block diagram illustrating an example regional oximetry device 200 for monitoring the autoregulation status of a patient. In the example shown in FIG. 2, regional oximetry device 200 is coupled to sensing device 250 and may be collectively referred to as a regional oximetry system, which each generate and process physiological signals of a subject. In some examples, sensing device 250 and regional oximetry device 200 may be part of an oximeter. As shown in FIG. 2, regional oximetry device 200 includes back-end processing circuitry 214, user interface 230, light drive circuitry 240, front-end processing circuitry 216, control circuitry 245, and communication interface 290. Regional oximetry device 200 may be communicatively coupled to sensing device 250. Regional oximetry device 200 is an example of regional oximetry device 100 shown in FIG. 1. In some examples, regional oximetry device 200 may also include a blood pressure sensor and/or a blood volume sensor (e.g., sensing devices 151 and 152 of FIG. 1).

In the example shown in FIG. 2, sensing device 250 includes light source 260, detector 262, and detector 263. In some examples, sensing device 250 may include more than two detectors. Light source 260 may be configured to emit photonic signals having two or more wavelengths (e.g., up to four or more wavelengths) of light (e.g., red and infrared (IR)) into a subject's tissue. For example, light source 260 may include a red light emitting light source and an IR light emitting light source, (e.g., red and IR LEDs), for emitting light into the tissue of a subject to generate physiological signals. In some examples, the red wavelength may be between about 600 nm and about 700 nm, and the IR wavelength may be between about 800 nm and about 1000 nm. Other wavelengths of light may be used in other examples. Light source 260 may include any number of light sources with any suitable characteristics. In examples in which an array of sensors is used in place of sensing device 250, each sensing device may be configured to emit a single wavelength. For example, a first sensing device may emit only a red light while a second sensing device may emit only an IR light. In some examples, light source 260 may be configured to emit two or more wavelengths of near-infrared light (e.g., wavelengths between 600 nm and 1000 nm) into a subject's tissue. In some examples, light source 260 may be configured to emit four wavelengths of light (e.g., 724 nm, 770 nm, 810 nm, and 850 nm) into a subject's tissue. In some examples, the subject may be a medical patient.

As used herein, the term "light" may refer to energy produced by radiative sources and may include one or more of ultrasound, radio, microwave, millimeter wave, infrared, visible, ultraviolet, gamma ray or X-ray electromagnetic radiation. Light may also include any wavelength within the radio, microwave, infrared, visible, ultraviolet, or X-ray spectra, and that any suitable wavelength of electromagnetic radiation may be appropriate for use with the present techniques. Detectors 262 and 263 may be chosen to be specifically sensitive to the chosen targeted energy spectrum of light source 260.

In some examples, detectors 262 and 263 may be configured to detect the intensity of multiple wavelengths of near-infrared light. In some examples, detectors 262 and 263 may be configured to detect the intensity of light at the red and IR wavelengths. In some examples, an array of detectors may be used and each detector in the array may be configured to detect an intensity of a single wavelength. In operation, light may enter detector 262 after passing through the subject's tissue, including skin, bone, and other shallow tissue (e.g., non-cerebral tissue and shallow cerebral tissue). Light may enter detector 263 after passing through the subject's tissue, including skin, bone, other shallow tissue (e.g., non-cerebral tissue and shallow cerebral tissue), and deep tissue (e.g., deep cerebral tissue). Detectors 262 and 263 may convert the intensity of the received light into an electrical signal. The light intensity may be directly related to the absorbance and/or reflectance of light in the tissue.

That is, when more light at a certain wavelength is absorbed or reflected, less light of that wavelength is received from the tissue by detectors 262 and 263.

After converting the received light to an electrical signal, detectors 262 and 263 may send the detection signals to regional oximetry device 200, where the detection signals may be processed and physiological parameters may be determined (e.g., based on the absorption of the red and IR wavelengths in the subject's tissue at both detectors). In some examples, one or more of the detection signals may be preprocessed by sensing device 250 before being transmitted to regional oximetry device 200. Additional example details of determining oxygen saturation based on light signals may be found in commonly assigned U.S. Pat. No. 9,861,317, which issued on Jan. 9, 2018, and is entitled "Methods and Systems for Determining Regional Blood Oxygen Saturation," the entire content of which is incorporated herein by reference.

Control circuitry 245 may be coupled to light drive circuitry 240, front-end processing circuitry 216, and back-end processing circuitry 214, and may be configured to control the operation of these components. In some examples, control circuitry 245 may be configured to provide timing control signals to coordinate their operation. For example, light drive circuitry 240 may generate one or more light drive signals, which may be used to turn on and off light source 260, based on the timing control signals provided by control circuitry 245. Front-end processing circuitry 216 may use the timing control signals to operate synchronously with light drive circuitry 240. For example, front-end processing circuitry 216 may synchronize the operation of an analog-to-digital converter and a demultiplexer with the light drive signal based on the timing control signals. In addition, the back-end processing circuitry 214 may use the timing control signals to coordinate its operation with front-end processing circuitry 216.

Light drive circuitry 240, as discussed above, may be configured to generate a light drive signal that is provided to light source 260 of sensing device 250. The light drive signal may, for example, control the intensity of light source 260 and the timing of when light source 260 is turned on and off. In some examples, light drive circuitry 240 provides one or more light drive signals to light source 260. Where light source 260 is configured to emit two or more wavelengths of light, the light drive signal may be configured to control the operation of each wavelength of light. The light drive signal may include a single signal or may comprise multiple signals (e.g., one signal for each wavelength of light).

Front-end processing circuitry 216 may perform any suitable analog conditioning of the detector signals. The conditioning performed may include any type of filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof. The conditioned analog signals may be processed by an analog-to-digital converter of circuitry 216, which may convert the conditioned analog signals into digital signals. Front-end processing circuitry 216 may operate on the analog or digital form of the detector signals to separate out different components of the signals. Front-end processing circuitry 216 may also perform any suitable digital conditioning of the detector signals, such as low pass, high pass, band pass, notch, averaging, or any other suitable filtering, amplifying, performing an operation on the signal, performing any other suitable digital conditioning, or any combination thereof. Front-end processing circuitry 216 may decrease the number of samples in the digital detector signals. In some examples, front-end processing circuitry 216 may also remove dark or ambient contributions to the received signal.

Back-end processing circuitry 214 may include processing circuitry 210 and memory 220. Processing circuitry 210 may include an assembly of analog or digital electronic components and may be configured to execute software, which may include an operating system and one or more applications, as part of performing the functions described herein with respect to, e.g., processing circuitry 110. Processing circuitry 210 may receive and further process one or more signals received from front-end processing circuitry 216. For example, processing circuitry 210 may determine physiological parameter values based on the received signals. For example, processing circuitry 210 may compute one or more of regional oxygen saturation, blood oxygen saturation (e.g., arterial, venous, or both), pulse rate, respiration rate, respiration effort, blood pressure, hemoglobin concentration (e.g., oxygenated, deoxygenated, and/or total), any other suitable physiological parameters, or any combination thereof.

Processing circuitry 210 may perform any suitable signal processing of a signal, such as any suitable band-pass filtering, adaptive filtering, closed-loop filtering, any other suitable filtering, and/or any combination thereof. Processing circuitry 210 may also receive input signals from additional sources not shown. For example, processing circuitry 210 may receive an input signal containing information about treatments provided to the subject from user interface 230. Additional input signals may be used by processing circuitry 210 in any of the determinations or operations it performs in accordance with back-end processing circuitry 214 or regional oximetry device 200.

Processing circuitry 210 is an example of processing circuitry 110 and is configured to perform the techniques of this disclosure. For example, processing circuitry 210 is configured to receive signals indicative of physiological parameters including a blood pressure of the patient. In some examples, processing circuitry 210 is also configured to determine autoregulation state values based on the received signals and determine that one of the autoregulation state values is anomalous. Processing circuitry 210 may be configured to modify the anomalous autoregulation state value based on other autoregulation state value. Processing circuitry 210 is also configured to determine an autoregulation status of the patient based on the autoregulation state values including the modified autoregulation state value. Processing circuitry 210 is also configured to determine a autoregulation status based on measured blood pressures and/or adjusted measured blood pressures due to a detected abrupt change in the measured blood pressures.

Memory 220 may include any suitable computer-readable media capable of storing information that can be interpreted by processing circuitry 210. In some examples, memory 220 may store reference absorption curves, reference sets, autoregulation state values including modified and unmodified values, correlation coefficient values, threshold rates, threshold values, smoothing functions, Gaussian filters, confidence metrics, expected autoregulation functions, historical patient data, physiological parameter values such as blood oxygen saturation, pulse rate, blood pressure, fiducial point locations or characteristics, initialization parameters, any other determined values, or any combination thereof, in a memory device for later retrieval. Memory 220 may also store thresholds for detecting abrupt changes in blood pressure, and so on. Back-end processing circuitry 214 may be communicatively coupled with user interface 230 and communication interface 290.

User interface 230 may include input device 234, display 232, and speaker 236 in some examples. User interface 230 is an example of user interface 130 shown in FIG. 1, and display 232 is an example of display 132 shown in FIG. 1. User interface 230 may include, for example, any suitable device such as one or more medical devices (e.g., a medical monitor that displays various physiological parameters, a medical alarm, or any other suitable medical device that either displays physiological parameters or uses the output of back-end processing 214 as an input), one or more display devices (e.g., monitor, personal digital assistant (PDA), mobile phone, tablet computer, clinician workstation, any other suitable display device, or any combination thereof), one or more audio devices, one or more memory devices, one or more printing devices, any other suitable output device, or any combination thereof.

Input device 234 may include any type of user input device such as a keyboard, a mouse, a touch screen, buttons, switches, a microphone, a joystick, a touch pad, or any other suitable input device or combination of input devices. In other examples, input device 234 may be a pressure-sensitive or presence-sensitive display that is included as part of display 232. Input device 234 may also receive inputs to select a model number of sensing device 250 (FIG. 2), or blood pressure processing equipment. In some examples, processing circuitry 210 may determine the type of presentation for display 232 based on user inputs received by input device 234. In some examples, processing circuitry 210 may also determine a threshold rate and/or a length of a window of time based on user input received from input device 234.

Figure 3:
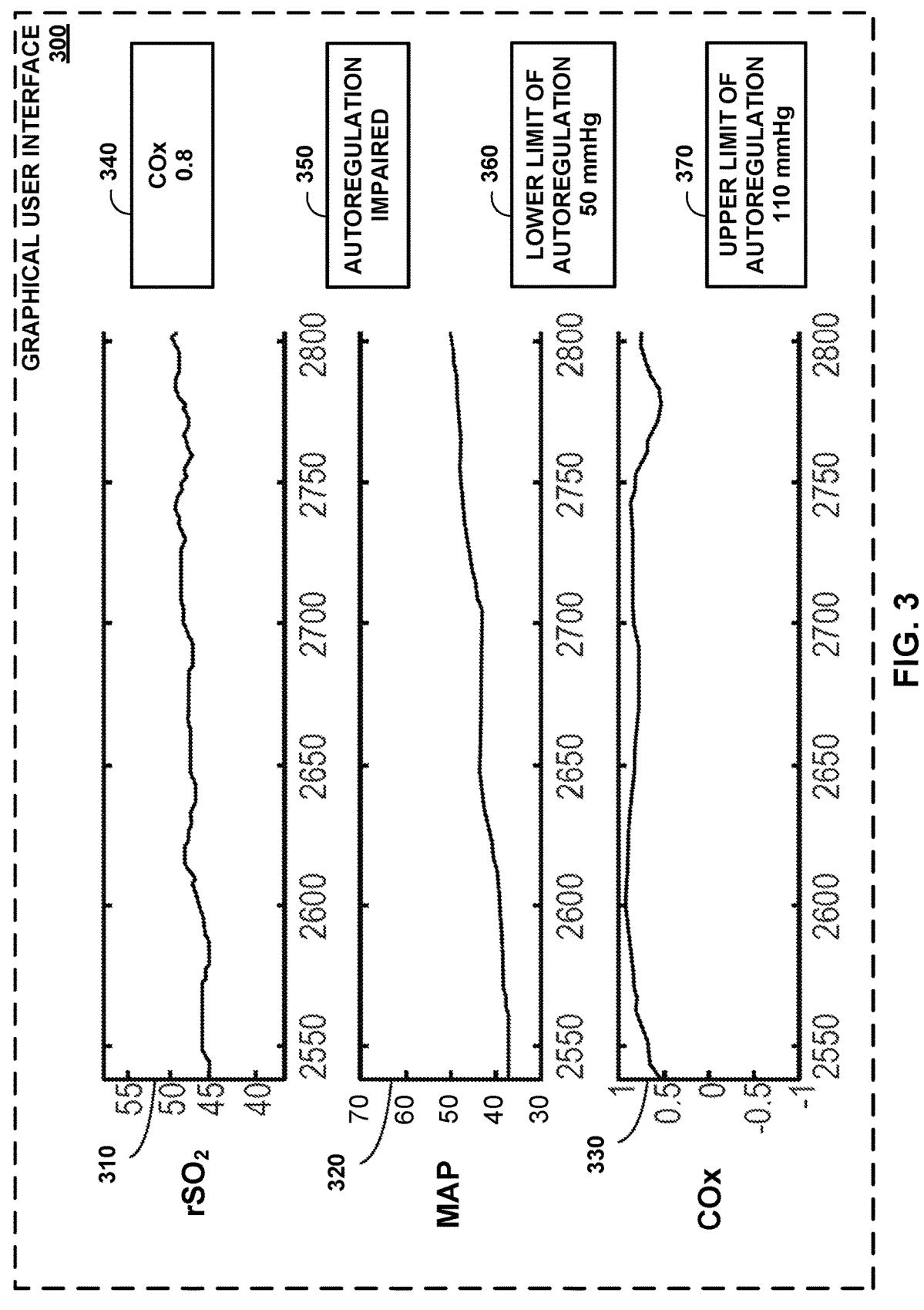
FIG. 3 illustrates an example graphical user interface including autoregulation information presented on a display.

In some examples, the patient may be a medical patient and display 232 may exhibit a list of values which may generally apply to the patient, such as, for example, an oxygen saturation signal indicator, a blood pressure signal indicator, a COx signal indicator, a COx value indicator, and/or an autoregulation status indicator. Display 232 may also be configured to present additional physiological parameter information. Graphical user interface 300 shown in FIG. 3 is an example of an interface that can be presented via display 232 of FIG. 2 under the control of processing circuitry 210. Additionally, display 232 may present, for example, one or more estimates of a subject's regional oxygen saturation generated by regional oximetry device 200 (referred to as an "rSO$_2$" measurement). Display 232 may also present indications of the upper and lower limits of cerebral autoregulation. In some examples, speaker 236 of user interface 230 may provide an audible sound that may be used in various examples, such as for example, sounding an audible notification in the event that a patient's physiological parameters are not within a predefined normal range and/or in the event that processing circuitry 210 determines that sensed blood pressure values may be inaccurate due to a non-physiological reason such as due to movement of a blood pressure probe of blood pressure sensor 151 (FIG. 1).

Communication interface 290 may enable regional oximetry device 200 to exchange information with external devices. Communication interface 290 may include any suitable hardware, software, or both, which may allow regional oximetry device 200 to communicate with electronic circuitry, a device, a network, a server or other workstations, a display, or any combination thereof. For example, regional oximetry device 200 may receive MAP (or other measured blood pressure) values and/or oxygen saturation values from an external device via communication interface 290.

The components of regional oximetry device 200 that are shown and described as separate components are shown and described as such for illustrative purposes only. In some examples the functionality of some of the components may be combined in a single component. For example, the functionality of front end processing circuitry 216 and back-end processing circuitry 214 may be combined in a single processor system. Additionally, in some examples the functionality of some of the components of regional oximetry device 200 shown and described herein may be divided over multiple components. For example, some or all of the functionality of control circuitry 245 may be performed in front end processing circuitry 216, in back-end processing circuitry 214, or both. In other examples, the functionality of one or more of the components may be performed in a different order or may not be required. In some examples, all of the components of regional oximetry device 200 can be realized in processor circuitry.

FIG. 3 illustrates an example graphical user interface 300 including autoregulation information presented on a display. FIG. 3 is an example of a presentation by processing circuitry 110 on display 132 shown in FIG. 1 or by processing circuitry 210 on display 232 shown in FIG. 2. Although FIG. 3 is described with respect to processing circuitry 110 of regional oximetry device 100 (FIG. 1), in other examples, processing circuitry 210, 214, and/or 216 (FIG. 2), alone or in combination with processing circuitry 110, may perform any part of the techniques of FIG. 3.

Graphical user interface 300 may be configured to display various information related to blood pressure, oxygen saturation, the COx index, limits of autoregulation, and/or autoregulation status. As shown, graphical user interface 300 may include oxygen saturation signal indicator 310, blood pressure signal indicator 320, and COx signal indicator 330. Graphical user interface 300 may include COx value indicator 340, autoregulation status indicator 350, and limit of autoregulation indicators 360 and 370.

Blood pressure signal indicator 320 may present a set of MAP values determined by processing circuitry 110 of regional oximetry device 100. The MAP values may be based on measured blood pressure values, but the raw measured blood pressure values (e.g., showing intra-cardia cycle variations) may be displayed in other examples. In some examples, blood pressure signal indicator 320 may present MAP values as discrete points over time or in a table. Blood pressure signal indicator 320 may also present MAP values as a moving average or waveform of discrete points. Blood pressure signal indicator 320 may present MAP values as a single value (e.g., a number) representing a current MAP value. Oxygen saturation signal indicator 310 and COx signal indicator 330 may also present rSO2 values and COx values, respectively, as discrete points, in a table, as a moving average, as a waveform, and/or as a single value. In other examples, the data from two or more of oxygen saturation signal indicator 310, blood pressure signal indicator 320, or COx signal indicator 330 may be combined together on a single graph.

COx signal indicator 330 may present a set of correlation coefficients determined by processing circuitry 110. Processing circuitry 110 may determine the correlation coefficients as a function of the oxygen saturation values presented in oxygen saturation signal indicator 310 and the MAP values presented in blood pressure signal indicator 320. In some examples, a COx value at or near one indicates the cerebral autoregulation status of a patient is impaired, as shown in autoregulation status indicator 350.

Processing circuitry 110 may determine a set of correlation coefficient values and associated blood pressure values using the values presented in indicators 310, 320, and/or 330. Processing circuitry 110 may determine autoregulation state values based on the correlation coefficient values associated with a range of blood pressure values. As the blood pressure of the patient changes, processing circuitry 110 can determine new correlation coefficient values at the most recent blood pressure value. Processing circuitry 110 can also determine an autoregulation state value for the most recent blood pressure value. Thus, processing circuitry 110 may be configured to update (or leave unchanged) the autoregulation state value at the most recent blood pressure value.

Processing circuitry 110 may be configured to determine an estimate of a limit of autoregulation based on the autoregulation state values across a range of blood pressure values. For example, processing circuitry 110 may determine a lower limit of autoregulation at forty millimeters of mercury based on the nearby correlation coefficient values (e.g., the correlation coefficient values from thirty to fifty millimeters of mercury). Thus, processing circuitry 110 may be configured to change or set autoregulation state values at or near the most recent blood pressure value.

In some examples, processing circuitry 110 may also be configured to identify and modify anomalous autoregulation state values, even if the anomalous autoregulation state values are separated from the current blood pressure value by more than five or ten millimeters of mercury. For example, processing circuitry 110 can identify an autoregulation state value as anomalous if the autoregulation state value represents a first autoregulation state and most or all of the nearby autoregulation state values represent another autoregulation state.

COx value indicator 340 shows a COx value determined by processing circuitry 110, which is shown as 0.8 in the example of FIG. 3 and may change over time. The COx value of 0.8 may result in a determination by processing circuitry 110 that the cerebral autoregulation status of the patient is impaired. Processing circuitry 110 may be configured to present, as the COx value in COx value indicator 340, the most recently determined COx value or a moving average of recent COx values. In order to determine the cerebral autoregulation status of a patient for presentation in autoregulation status indicator 350, processing circuitry 110 may determine whether the most recent MAP value shown in blood pressure signal indicator 320 is between the limits of cerebral autoregulation presented in limit of autoregulation indicators 360 and 370. In examples in which processing circuitry 110 determines that the current autoregulation status is impaired, processing circuitry 110 may be configured to set the autoregulation value associated with the current blood pressure value of the patient to a value representing an impaired autoregulation state. Processing circuitry 110 can also present a color such as green (e.g., for intact autoregulation) or red (e.g., for impaired autoregulation) to help aid a user's understanding of an autoregulation status of the patient.

In some examples, processing circuitry 110 may present limit of autoregulation indicators 360 and/or 370 in terms of blood pressure, for example, in units of millimeters of mercury (mmHg). Processing circuitry 110 can determine the limits of cerebral autoregulation (LLA and ULA) for presentation in indicators 360 and 370 based on a relationship between the blood pressure of a patient and another physiological parameter of the patient. For example, processing circuitry 110 can highlight indicator 350 and/or indicator 360 when the most recent blood pressure of the patient is outside of the LLA, or processing circuitry 110 can highlight indicator 350 and/or 370 when the most recent blood pressure of the patient is outside of the ULA. For example, indicator 360 may be highlighted when the LLA has been exceeded or indicator 360 may be highlighted when the ULA has been exceeded. In other examples, a single indicator may present the type of limit that has been exceed by the MAP value. If the LLA or ULA change, processing circuitry 110 may control user interface 300 to change the value of the LLA or ULA in accordance with any change to that respective value.

Processing circuitry 110 may determine an estimate of a lower limit of autoregulation presented in indicator 360 and/or an estimate of an upper limit of autoregulation presented in indicator 370. Processing circuitry 110 may determine the estimates based on a set of correlation coefficient values including one or more updated values. Processing circuitry 110 may be configured to generate a notification in response to determining that the MAP value is less than or equal to the estimate of the lower limit of autoregulation. Processing circuitry 110 may output the notification in autoregulation status indicator 350 as text, color, blinking, and/or any other suitable visible or audible manner.

In some examples, processing circuitry 110 may be configured to determine that an autoregulation state value outside of the limits of autoregulation represents an intact autoregulation state. In the example of FIG. 3, blood pressure values less than fifty millimeters of mercury and greater than one hundred and ten millimeters of mercury are outside of the limits of autoregulation. Processing circuitry 110 may determine an autoregulation state value representing an intact autoregulation state at a blood pressure value outside of the limits of autoregulation, such as at thirty millimeters of mercury. Processing circuitry 110 may be configured to identify the autoregulation state value associated with thirty millimeters of mercury as anomalous because the lower limit of autoregulation is greater than thirty millimeters of mercury, and yet the autoregulation state value has been designated as representing an intact autoregulation state. Responsive to determining that the autoregulation state value associated with thirty millimeters of mercury is anomalous, processing circuitry 110 may be configured to set the autoregulation state value associated with thirty millimeters of mercury to an autoregulation state value representing an impaired autoregulation state.

Similarly, processing circuitry 110 may determine an autoregulation state value representing an impaired autoregulation state at a blood pressure value inside of the limits of autoregulation, which is between fifty and one hundred and ten millimeters of mercury in the example of FIG. 3. Processing circuitry 110 may be configured to identify an autoregulation state value associated with seventy millimeters of mercury as anomalous because the lower limit of autoregulation is less than seventy millimetres of mercury, the upper limit of autoregulation is greater than seventy millimetres of mercury, and yet has been designated as representing an impaired autoregulation state. Responsive to determining that the autoregulation state value associated with seventy millimeters of mercury is anomalous, processing circuitry 110 may be configured to set the autoregulation state value associated with seventy millimeters of mercury to an autoregulation state value representing an intact autoregulation state.

Figure 4:
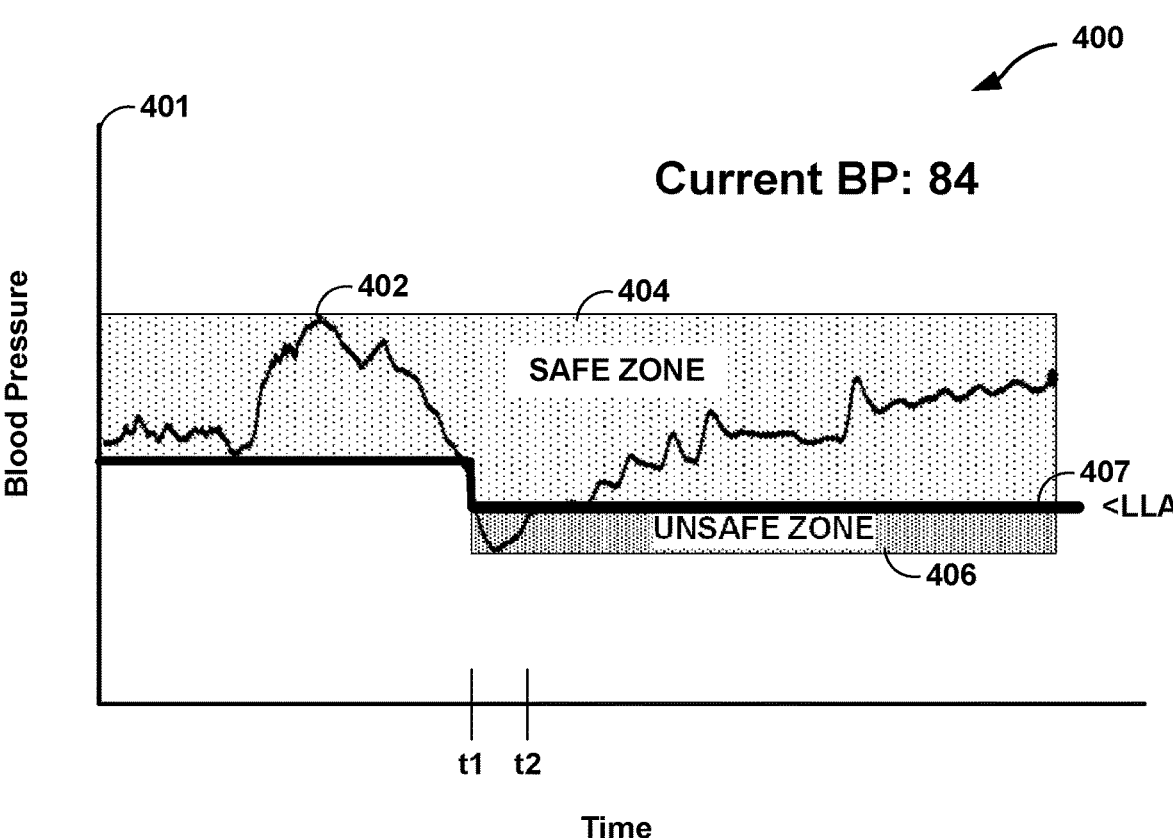
FIG. 4 illustrates an example user interface that includes autoregulation information.

FIG. 4 illustrates an example user interface that includes autoregulation information. As shown in FIG. 4, processing circuitry 110 of regional oximetry device 100 or processing circuitry 210 of regional oximetry device 200 may output, for display at display 132 or display 232, an interface, such as graphical user interface (GUI) 400, that indicates the autoregulation status of a patient.

In some examples, GUI 400 outputted by processing circuitry 110 or processing circuitry 210 may include graph 401 of blood pressure value 402 of a patient over time. Time is represented along the x-axis of graph 401 and blood pressure is represented along the y-axis of graph 401. As such, blood pressure value 402 in graph 401 indicates both the current blood pressure of the patient as well as the past blood history of the patient. The state vector or plurality of autoregulation state values at any time represents and can be considered as a slice or cross-section of graph 104 in the y-axis direction.

GUI 400 outputted by processing circuitry 110 and processing circuitry 210 may include indications of the autoregulation status of the patient over time. Specifically, GUI 400 may include indications of whether the patient is, at a point in time, in an intact autoregulation state or in an impaired autoregulation state. To indicate the autoregulation status of the patient, GUI 400 may include graphical indication 407 of the LLA of the patient. In some examples, blood pressure value 402 being above the graphical indication 407 of the LLA of the patient in graph 401 may indicate that the patient is in an intact autoregulation state, while blood pressure value 402 being below the graphical indication 407 of the LLA of the patient in graph 401 may indicate that the patient is in an intact autoregulation state.

GUI 400 may include an indication of the LLA of the patient but may not include the ULA of the patient. That is, in some examples, GUI 400 includes graphical indication 407 of the LLA of the patient but not include a graphical indication of the ULA of the patient. While an indication of the LLA may be useful to clinicians monitoring the autoregulation status of the patient to determine whether the patient is in an intact autoregulation state or in an impaired autoregulation state by watching whether the blood pressure value of the patient, the ULA may not provide much useful information to the clinician. In fact, including a graphical indication of the ULA of the patient in GUI 400 may distract clinicians from monitoring the autoregulation status of the patient.

GUI 400 may include a graphical indication of whether the autoregulation status of the patient is in an intact autoregulation state or in an impaired autoregulation state. Specifically, when processing circuitry 110 or processing circuitry 210 determines that the patient is in an intact autoregulation state at a point in time, GUI 400 may include a graphical representation of the patient being in an intact autoregulation state at the point in time. Similarly, when processing circuitry 110 or processing circuitry 210 determines that the patient is in an impaired autoregulation state at a point in time, GUI 400 may include a graphical representation of the patient being in an impair state at the point in time, where the graphical representation of the patient being in an intact autoregulation state is visually different from the graphical representation of the patient being in an impaired autoregulation state.

For example, GUI 400 outputted by processing circuitry 110 or processing circuitry 210 may include, in graph 401 safe zone 404 that is a graphical representation of an intact autoregulation state and unsafe zone 406 that is a graphical representation of an impaired autoregulation state. Specifically, safe zone 404 may be the region of graph 401 above the LLA of the patient, and unsafe zone 406 may be the region of graph 401 below the LLA of the patient. At any point in time, blood pressure value 402 being in safe zone 404 may indicate that the patient is in an intact autoregulation state. Similarly, at any point in time, blood pressure value 402 being in unsafe zone 406 may indicate that the patient is in an impaired autoregulation state. In this way, GUI 400 may include a graphical indication of the autoregulation status of the patient over time.

In some examples, GUI 400 may use colors to indicate the autoregulation states of the patient, and may use different colors to indicate different autoregulation states for the patient. For example, GUI 400 may use a green color for autoregulation state values representing an intact autoregulation state, a red color for autoregulation state values representing an impaired autoregulation state, and a black color for autoregulation state values representing an uncategorized autoregulation state. As such, safe zone 404 in GUI 400 may be of a different color than unsafe zone 406. For example, safe zone 404 may be of a green color in GUI 400 and unsafe zone 406 may be of a red color in GUI 400. FIG. 4 depicts these colors in greyscale as different shades of grey.

In some examples, while monitoring the autoregulation status of the patient, processing circuitry 110 or processing circuitry 210 may determine a change (e.g., an increase or a decrease) in a limit of autoregulation, such as a change in the LLA. Processing circuitry 110 or processing circuitry 210 may be configured to, in response to determining a change in a limit of autoregulation, update GUI 400 based at least in part on the change in the limit of autoregulation.

For example, processing circuitry 110 or processing circuitry 210 may be configured to, in response to determining a change in a limit of autoregulation at a point in time, update the portion of the graphical representation of the autoregulation state that is prior to the change in the limit of autoregulation, to indicate a decrease in the confidence of the autoregulation state of the patient determined by processing circuitry 110 or processing circuitry 210 prior to the point in time. For example, processing circuitry 110 or processing circuitry 210 may update the portion of safe zone 404 that is prior in time to the point in time and/or update the portion of unsafe zone 406 that is prior in time to the point in time. That is, because a change in the limit of autoregulation at a point in time may indicate a possibility that the limit of autoregulation prior to the point in time was incorrectly determined, it may be possible that the autoregulation state of the patient determined by processing circuitry 110 or processing circuitry 210 prior to the point in time is incorrect.

In some examples, processing circuitry 110 or processing circuitry 210 may be configured to, in response to determining a change in a limit of autoregulation at a point in time, change the intensity of the color(s) used by GUI 400, prior to the change in the limit of autoregulation, to indicate the updated autoregulation states of the patient prior to the point in time. For example, processing circuitry 110 or processing circuitry 210 may change the intensity of the color(s) used by GUI 400 to represent the autoregulation state of the patient prior to the point in time based on the magnitude (e.g., amount) of the determined change in the limit of autoregulation.

In the example of FIG. 4, the LLA changes at time t1. In response to determining a relatively large change in a limit of autoregulation at time t1, processing circuitry 110 or processing circuitry 210 may reduce the intensity of the color (e.g., green color) presented in the region of safe zone 404 prior to time t1 by a relatively large amount that corresponds to the magnitude of the determined change in the limit of autoregulation at time t1. The less intense color may indicate lower confidence in the estimates of, for example the LLA.

Similarly, in response to determining a relatively small change in a limit of autoregulation at time t1, processing circuitry 110 or processing circuitry 210 may reduce the intensity of the color presented in the region of safe zone 404 prior to time t1 by a relatively small amount that corresponds to the magnitude of the determined change in the limit of autoregulation at time t1. In another example, in response to determining no change in a limit of autoregulation at time t1, processing circuitry 110 or processing circuitry 210 may refrain from changing the intensity of the color presented in the region of safe zone 404 prior to time t1.

Thus, with respect to safe zone 404, a large change in a limit of autoregulation at time t1 may result in a much dimmer color of the region of safe zone 404 prior to time t1, a small change in a limit of autoregulation may result in a slightly dimmer color of the region of safe zone 404 prior to time t1, and no change in the limits of autoregulation may result in a brighter color or no change in the color of the region of safe zone 404 prior to time t1.

Similarly, processing circuitry 110 or processing circuitry 210 may use similar techniques to change the color (e.g., red color) in the unsafe zone 406. For example, in response to determining a relatively large change in a limit of autoregulation at time t2, processing circuitry 110 or processing circuitry 210 may reduce the intensity of the color presented in the region of unsafe zone 406 prior to time t2 by a relatively large amount that corresponds to the magnitude of the determined change in the limit of autoregulation at time t2.

In another example, in response to determining a relatively small change in a limit of autoregulation at time t2, processing circuitry 110 or processing circuitry 210 may reduce the intensity of the color presented in the region of unsafe zone 406 prior to time t2 by a relatively small amount that corresponds to the magnitude of the determined change in the limit of autoregulation at time t2. In another example, in response to determining no change in a limit of autoregulation at time t2, processing circuitry 110 or processing circuitry 210 may refrain from changing the intensity of the color presented in the region of unsafe zone 406 prior to time t2.

FIG. 5 is a flow diagram illustrating an example technique for presenting the autoregulation status of a patient. Although FIG. 5 is described with respect to regional oximetry device 100 (FIG. 1), in other examples, other devices may perform any part of the technique of FIG. 5. For example, processing circuitry 210, 214, and/or 216 (FIG. 2), alone or in combination with processing circuitry 110, may perform any part of the technique of FIG. 5.

In the example of FIG. 5, processing circuitry 110 may receive one or more signals of a patient (502). Processing circuitry 110 may determine an autoregulation status of the patient based at least in part on the one or more signals (504). Processing circuitry 110 may output, for display at an output device, a graphical user interface (GUI) that includes an indication of the autoregulation status of the patient and an indication of a lower limit of autoregulation (LLA) value, wherein the GUI does not include an indication of an upper limit of autoregulation (ULA) value (506).

This disclosure includes the following examples.

Example 1: A method includes receiving, by processing circuitry, one or more signals of a patient; determining, by the processing circuitry, an autoregulation status of the patient based at least in part on the one or more signals; and outputting, by the processing circuitry and for display at an output device, a graphical user interface (GUI) that includes an indication of the autoregulation status of the patient and an indication of a lower limit of autoregulation (LLA) value, wherein the GUI does not include an indication of an upper limit of autoregulation (ULA) value.

Example 2: The method of example 1, wherein the autoregulation status of the patient includes a first graphical indication of a safe zone associated with an intact autoregulation state of the patient and a second graphical indication of an unsafe zone associated with an impaired autoregulation state of the patient.

Example 3: The method of example 2, wherein: the safe zone is a first region of the GUI above the indication of the LLA; and the unsafe zone is a second region of the GUI below the indication of the LLA.

Example 4: The method of any of examples 2 and 3, wherein the first graphical indication of the safe zone in the GUI is of a first color in the GUI and wherein the second graphical indication of the safe zone in the GUI is of a second color different from the first color.

Example 5: The method of any of examples 2-4, further includes determining, by the processing circuitry, a change in the LLA at a point in time; and in response to determining the change in the LLA at the point in time, updating, by the processing circuitry, at least one of: a portion of the first graphical indication of the safe zone that is prior to the point in time or a portion of the second graphical representation of the safe zone that is prior to the point in time.

Example 6: The method of example 5, wherein updating at least one of: the portion of the first graphical indication of the safe zone that is prior to the point in time or the portion of the second graphical representation of the safe zone that is prior to the point in time further comprises: updating, by the processing circuitry, the portion of the first graphical indication of the safe zone that is prior to the point in time or the portion of the second graphical representation of the safe zone that is prior to the point in time based at least in part on an amount of the change in the LLA at the point in time.

Example 7: The method of any of examples 5 and 6, wherein updating at least one of: the portion of the first graphical indication of the safe zone that is prior to the point in time or the portion of the second graphical representation of the safe zone that is prior to the point in time further comprises: updating, by the processing circuitry, a color of at least one of: the portion of the first graphical indication of the safe zone that is prior to the point in time or the portion of the second graphical representation of the safe zone that is prior to the point in time.

Example 8: The method of any of examples 5-7, wherein updating at least one of: the portion of the first graphical indication of the safe zone that is prior to the point in time or the portion of the second graphical representation of the safe zone that is prior to the point in time further comprises: updating, by the processing circuitry, a color intensity of at least one of: the portion of the first graphical indication of the safe zone that is prior to the point in time or the portion of the second graphical representation of the safe zone that is prior to the point in time.

Example 9: A system includes one or more sensing devices; and processing circuitry configured to: receive, from the one or more sensing devices, one or more signals of a patient; determine an autoregulation status of the patient based at least in part on the one or more signals; and output, for display at an output device, a graphical user interface (GUI) that includes an indication of the autoregulation status of the patient and an indication of a lower limit of autoregulation (LLA) value, wherein the GUI does not include an indication of an upper limit of autoregulation (ULA) value.

Example 10: The system of example 9, wherein the autoregulation status of the patient includes a first graphical indication of a safe zone associated with an intact autoregulation state of the patient and a second graphical indication of an unsafe zone associated with an impaired autoregulation state of the patient.

Example 11: The system of example 10, wherein: the safe zone is a first region of the GUI above the indication of the LLA; and the unsafe zone is a second region of the GUI below the indication of the LLA.

Example 12: The system of any of examples 10 and 11, wherein the first graphical indication of the safe zone in the GUI is of a first color in the GUI and wherein the second graphical indication of the safe zone in the GUI is of a second color different from the first color.

Example 13: The system of any of examples 10-12, wherein the processing circuitry is further configured to: determine, a change in the LLA at a point in time; and in response to determining the change in the LLA at the point in time, update at least one of: a portion of the first graphical indication of the safe zone that is prior to the point in time or a portion of the second graphical representation of the safe zone that is prior to the point in time.

Example 14: The system of example 13, wherein to update at least one of: the portion of the first graphical indication of the safe zone that is prior to the point in time or the portion of the second graphical representation of the safe zone that is prior to the point in time, the processing circuitry is further configured to: update the portion of the first graphical indication of the safe zone that is prior to the point in time or the portion of the second graphical representation of the safe zone that is prior to the point in time based at least in part on an amount of the change in the LLA at the point in time.

Example 15: The system of any of examples 13 and 14, wherein to update at least one of: the portion of the first graphical indication of the safe zone that is prior to the point in time or the portion of the second graphical representation of the safe zone that is prior to the point in time, the processing circuitry is further configured to: update a color of at least one of: the portion of the first graphical indication of the safe zone that is prior to the point in time or the portion of the second graphical representation of the safe zone that is prior to the point in time.

Example 16: The system of any of examples 13-15, wherein to update at least one of: the portion of the first graphical indication of the safe zone that is prior to the point in time or the portion of the second graphical representation of the safe zone that is prior to the point in time, the processing circuitry is further configured to: update a color intensity of at least one of: the portion of the first graphical indication of the safe zone that is prior to the point in time or the portion of the second graphical representation of the safe zone that is prior to the point in time.

Example 17: The system of any of examples 9-15, wherein the system includes the output device.

Example 18: A non-transitory computer readable storable medium includes receive one or more signals of a patient; determine an autoregulation status of the patient based at least in part on the one or more signals; and output, for display at an output device, a graphical user interface (GUI) that includes an indication of the autoregulation status of the patient and an indication of a lower limit of autoregulation (LLA) value, wherein the GUI does not include an indication of an upper limit of autoregulation (ULA) value.

Example 19: The non-transitory computer readable storable medium of example 18, wherein the autoregulation status of the patient includes a first graphical indication of a safe zone associated with an intact autoregulation state of the patient and a second graphical indication of an unsafe zone associated with an impaired autoregulation state of the patient.

Example 20: The non-transitory computer readable storable medium of example 19, wherein: the safe zone is a first region of the GUI above the indication of the LLA; and the unsafe zone is a second region of the GUI below the indication of the LLA.

The techniques described in this disclosure, including those attributed to devices 100 and 200, processing circuitry 110, 210, 214, and 216, memories 120 and 220, displays 132 and 232, sensing circuitries 140-142, circuitries 240 and 245, sensing devices 150, 151, 152, and 250, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in patient monitors, such as multiparameter patient monitors (MPMs) or other devices, remote servers, or other devices. The term "processor" or "processing circuitry" may generally refer to any of the foregoing logic circuitry, alone or in combination with other logic circuitry, or any other equivalent circuitry.

As used herein, the term "circuitry" refers to an ASIC, an electronic circuit, a processor (shared, dedicated, or group) and memory that execute one or more software or firmware programs, a combinational logic circuit, or other suitable components that provide the described functionality. The term "processing circuitry" refers one or more processors distributed across one or more devices. For example, "processing circuitry" can include a single processor or multiple processors on a device. "Processing circuitry" can also include processors on multiple devices, wherein the operations described herein may be distributed across the processors and devices.

Such hardware, software, firmware may be implemented within the same device or within separate devices to support the various operations and functions described in this disclosure. For example, any of the techniques or processes described herein may be performed within one device or at least partially distributed amongst two or more devices, such as between devices 100 and 200, processing circuitry 110, 210, 214, and 216, memories 120 and 220, sensing circuitries 140-142, and/or circuitries 240 and 245. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a non-transitory computer-readable storage medium encoded with instructions. Instructions embedded or encoded in an article of manufacture including a non-transitory computer-readable storage medium encoded, may cause one or more programmable processors, or other processors, to implement one or more of the techniques described herein, such as when instructions included or encoded in the non-transitory computer-readable storage medium are executed by the one or more processors. Example non-transitory computer-readable storage media may include RAM, ROM, programmable ROM (PROM), erasable programmable ROM (EPROM), electronically erasable programmable ROM (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache). Elements of devices and circuitry described herein, including, but not limited to, devices 100 and 200, processing circuitry 110, 210, 214, and 216, memories 120 and 220, displays 132 and 232, sensing circuitries 140-142, circuitries 240 and 245, sensing devices 150-152 and 250 may be programmed with various forms of software. The one or more processors may be implemented at least in part as, or include, one or more executable applications, application modules, libraries, classes, methods, objects, routines, subroutines, firmware, and/or embedded code, for example.

Various examples of the disclosure have been described. Any combination of the described systems, operations, or functions is contemplated. These and other examples are within the scope of the following claims.

What is claimed is:

1. A method comprising:

receiving, by processing circuitry, a blood pressure signal comprising blood pressure values of a patient;

determining, by the processing circuitry, an autoregulation status of the patient based at least in part on the blood pressure signal;

displaying a graphical user interface (GUI) that includes a graph of the blood pressure values over time and an indication on the graph of the autoregulation status of the patient and an indication of a lower limit of autoregulation (LLA) at a first time, the LLA comprising a first blood pressure value below which autoregulation is impaired, wherein the autoregulation status of the patient on the graph includes a first graphical indication of a safe zone associated with an intact autoregulation state of the patient above the LLA and a second graphical indication of an unsafe zone associated with an impaired autoregulation state of the patient below the LLA;

determining, by the processing circuitry, a change in the LLA at a second, subsequent time; and in response to determining the change in the LLA, updating the GUI, by the processing circuitry, wherein updating the GUI comprises visually changing:

the indication of the LLA on the graph to an updated value of the LLA based on the change, and a portion of the first graphical indication of the safe zone that is prior to the change in the LLA, a portion of the second graphical indication of the unsafe zone that is prior to the change in the LLA, or both.

2. The method of claim 1, wherein:

the safe zone is a first region of the GUI above the indication of the LLA; and the unsafe zone is a second region of the GUI below the indication of the LLA.

3. The method of claim 1, wherein the first graphical indication of the safe zone in the GUI is of a first color in the GUI, and wherein the second graphical indication of the unsafe zone in the GUI is of a second color different from the first color.

4. The method of claim 1, wherein updating the portion of the first graphical indication of the safe zone that is prior to the change in the LLA, the portion of the second graphical indication of the unsafe zone that is prior to the change in the LLA, or both comprises:

updating, by the processing circuitry, the portion of the first graphical indication of the safe zone that is prior to the or change in the LLA, the portion of the second graphical indication of the unsafe zone that is prior to the change in the LLA, or both based at least in part on an amount of the change in the LLA.

5. The method of claim 1, wherein updating the portion of the first graphical indication of the safe zone that is prior to change in the LLA, the portion of the second graphical indication of the unsafe zone that is prior to the change in the LLA, or both comprises:

updating, by the processing circuitry, a color of the portion of the first graphical indication of the safe zone that is prior to change in the LLA, a color of the portion of the second graphical indication of the unsafe zone that is prior to the change in the LLA, or both.

6. The method of claim 1, wherein updating the portion of the first graphical indication of the safe zone that is prior to the change in the LLA, the portion of the second graphical indication of the unsafe zone that is prior to the change in the LLA, or both comprises:

updating, by the processing circuitry, a color intensity of the portion of the first graphical indication of the safe zone that is prior to the change in the LLA, a color intensity of the portion of the second graphical indication of the unsafe zone that is prior to the change in the LLA, or both.

7. The method of claim 1, wherein updating, by the processing circuitry, the indication of the LLA comprises adjusting the graphical indication of the LLA from a first position that corresponds to the first blood pressure value to a second position that corresponds to a second blood pressure value.

8. The method of claim 1, comprising:

refraining, by the processing circuitry, from presenting an indication of an upper limit of autoregulation (ULA) comprising an upper blood pressure value above which autoregulation is impaired, such that the GUI does not include the indication of the ULA.

9. The method of claim 8, comprising refraining, by the processing circuitry, from presenting the indication of the ULA value in the GUI during a patient monitoring session, such that the GUI does not include the indication of the ULA during the patient monitoring session.

10. A system comprising:

a blood pressure sensor; and processing circuitry configured to:

receive, from the blood pressure sensor, a blood pressure signal comprising blood pressure values of a patient;

determine an autoregulation status of the patient based at least in part on the blood pressure signal;

display a graphical user interface (GUI) that includes a graph of the blood pressure values over time and an indication on the graph of the autoregulation status of the patient and an indication of a lower limit of autoregulation (LLA) at a first time, the LLA comprising a blood pressure value below which autoregulation is impaired, wherein the autoregulation status of the patient on the graph includes a first graphical indication of a safe zone associated with an intact autoregulation state of the patient above the LLA and a second graphical indication of an unsafe zone associated with an impaired autoregulation state of the patient below the LLA;

determine a change in the LLA at a second, subsequent time; and in response to determining the change in the LLA, update the indication of the LLA and update a portion of the first graphical indication of the safe zone that is prior to the change in the LLA, a portion of the second graphical indication of the unsafe zone that is prior to the change in the LLA, or both.

11. The system of claim 10, wherein the autoregulation status of the patient includes a first graphical indication of a safe zone associated with an intact autoregulation state of the patient and a second graphical indication of an unsafe zone associated with an impaired autoregulation state of the patient.

12. The system of claim 11, wherein:

the safe zone is a first region of the GUI above the indication of the LLA; and the unsafe zone is a second region of the GUI below the indication of the LLA.

13. The system of claim 10, wherein the system includes the display.

14. A non-transitory computer readable storage medium comprising instructions that, when executed, cause processing circuitry to:

receive a blood pressure signal comprising blood pressure values of a patient;

determine an autoregulation status of the patient based at least in part on the blood pressure signal;

display a graphical user interface (GUI) that includes a graph of the blood pressure values over time and an indication on the graph of the autoregulation status of the patient and an indication of a lower limit of autoregulation (LLA) at a first time, the LLA comprising a first blood pressure value below which autoregulation is impaired, wherein the autoregulation status of the patient on the graph includes a first graphical indication of a safe zone associated with an intact autoregulation status of the patient above the LLA and a second graphical indication of an unsafe zone associated with an impaired autoregulation status of the patient below the LLA;

determine a change in the LLA at a second, subsequent
  time; and in response to determining the change in the LLA, update
  the indication of the LLA and update a portion of the
  first graphical indication of the safe zone that is prior to
  the change in the LLA.

* * * * *